United States Patent [19]

McCaffrey et al.

[11] Patent Number: 4,576,948

[45] Date of Patent: Mar. 18, 1986

[54] COMPOSITION AND METHOD FOR INHIBITING TERMINAL DEOXYRIBONUCLEOTIDYL TRANSFERASE ACTIVITY

[75] Inventors: Ronald McCaffrey, Needham; George Wright, Worcester; Earl F. Baril, Rutland, all of Mass.

[73] Assignee: Trustees Boston University, Boston, Mass.

[21] Appl. No.: 459,433

[22] Filed: Jan. 20, 1983

[51] Int. Cl.[4] ................... A61K 31/505; C07D 239/54
[52] U.S. Cl. ................... 514/274; 514/908; 544/312
[58] Field of Search ......................... 424/251

[56] References Cited

PUBLICATIONS

Wright et al, Journal of Med. Chemistry, vol. 23 (1), (Jan. 1980) pp. 34–38.

Paul et al, Chemical Abstracts, vol. 61, (1964), 5642(g)–5643(a).

Primary Examiner—Donald G. Daus
Assistant Examiner—S. Kapner
Attorney, Agent, or Firm—Paul J. Cook; Lawrence Gilbert

[57] ABSTRACT

New uracil compounds having the formula:

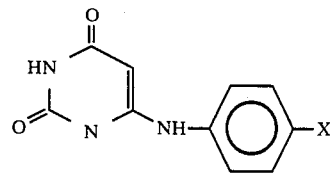

wherein X is $C_1$–$C_{10}$ alkoxy or amino are provided. These compounds are useful in treating patients having leukemia, the cells of which express terminal deoxynucleootidyl transferase.

4 Claims, 1 Drawing Figure

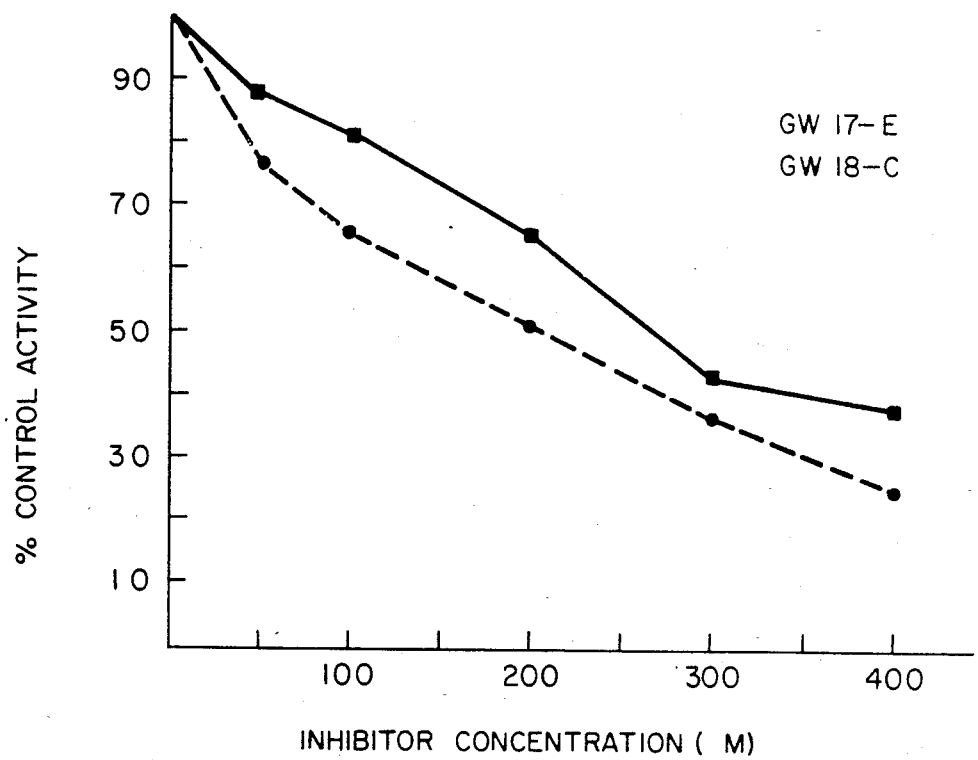

COMPOSITION AND METHOD FOR INHIBITING TERMINAL DEOXYRIBONUCLEOTIDYL TRANSFERASE ACTIVITY

This application is a continuation application of PCT US81 00721, filed May 29, 1981.

BACKGROUND OF THE INVENTION

This invention relates to a composition and method for inhibiting the activity of terminal deoxyribonucleotidyl transferase (TdT).

At the present time, there are four clasess of DNA mammolian polymerases which function to promote the production of DNA cells. Three of the DNA polymerases, known as alpha, beta or gamma DNA polymerase, require a template strand of DNA and a primer strand of DNA in order to effect the addition of substrates on the primer strand by addition of monophosphate residues at the 3-prime-OH end of the primer strand according to the Watson-Crick base pairing rule as dictated by the template strand. These DNA polymerases are known as replicative DNA polymerases. TdT polymerase differs from replicative DNA polymerases in that it requires only a single stranded DNA initiator molecule upon which to initiate synthesis. The TdT catalyzes the polymerization of deoxyribonucleotide on a 3-prime-OH end of oligo or polydeoxyribonucleotide initiators in the absence of the template.

Under normal conditions, TdT is present only in thymus and bone marrow with the highest concentrations being found in the thymocytes. From this observation, it has been postulated that TdT plays a role in immunodifferentiation, at least in the T-cell series. It has also been reported by McCaffrey et al in Proc. Acad. Sci. USA, vol. 70, No. 2, pp. 521–525, February 1973, that TdT is present in lymphoblastic leukemia cells. Furthermore, it has been found that TdT is not present in myeloblastic leukemia cells or lymphosarcoma-cell leukemia. While all patients having acute lymphoblastic leukemia do not test positively for TdT, the vast majority, about 95% of such patients, test positively for TdT. Accordingly, conventional biochemical techniques or fluorescent antibody labeling techniques for the TdT marker can be utilized to provide at least a preliminary test to determine the presence or absence of acute lymphoblastic leukemia cells in patients.

It has been proposed to utilize selective inhibitors of replicative DNA polymerases in order to inhibit replication of gram-positive bacteria. 6-(arylhydrazino) and 6-(arylamino) uracils have been found to be selective inhibitors of DNA replication by inhibiting bacterial DNA polymerase III. It is believed that the mechanism involves the specific pairing of substituents of the uracil moiety with template cytosine and binding of the 6-aryl group and its substituents to the polymerase, thereby sequestering the polymerase in a relatively stable protein:drug complex. It has been found that only a narrow spectrum of enzymes—the type III polymerases of gram-positive bacteria is susceptible to these uracil inhibitors. This is because the polymerase III possesses, at a critical location near the active site, a unique aryl site which strongly binds a 6-aryl moiety. It has been shown that the compound 6-(p-n-butylanilino) uracil is a specific inhibitor of DNA polymerase alpha of HeLa leukemia cells and, in vivo, is a selective inhibitor of HeLa cell division and DNA synthesis. No other mammalian cell DNA polymerase is inhibited by this compound.

It would be desirable to provide inhibitors of TdT in order to inhibit the growth of and/or cause the destruction of lymphoblastic leukemia cells in vivo or in vitro.

SUMMARY OF THE INVENTION

This invention is based upon the discovery that compounds having the formula:

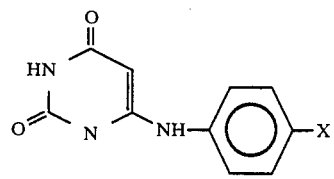

wherein X is $C_1$–$C_{10}$ alkoxy or amino and is effective for the selective inhibition of TdT for producing DNA. The novel compounds of this invention are prepared by reacting a 6-halo uracil with a compound of the formula:

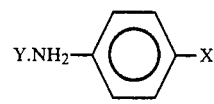

wherein Y is a solubilizing moiety such as hydrogen chloride.

DETAILED DESCRIPTION OF SPECIFIC EMBODIMENTS

The present invention provides novel compounds having the formula:

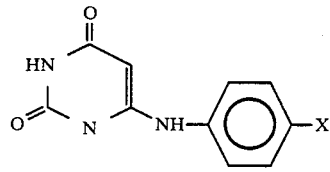

wherein X is $C_1$–$C_{10}$ alkoxy or amino and is effective for the selective inhibition of TdT for producing DNA.

The compounds of this invention are prepared by reacting a 6-halo uracil compound with the compound of the formula:

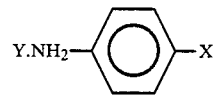

wherein Y is a solubilizing moiety such as hydrogen chloride. The reaction is conducted in an inert solvent such as glyme or the like under conditions to reflux the reaction mixture. Generally, the reaction is conducted for a period of time between about 3 and about 8 hours, preferably between about 3.5 and about 4.5 hours. The reaction mixture then is recovered and chilled to a temperature such that the reaction product precipitates from the reaction mixture and is recovered such as by filtration. The solid reaction product can then be purified such as by recrystallization.

The compounds of this invention are useful in the therapeutic treatment of patients afflicted with acute lymphoblastic leukemia (ALL) and can be administered either alone or in combination with pharmaceutically acceptable carriers. The proportion of active ingredient to carrier is determined by the solubility and chemical nature of the compound, chosen route of administration and standard pharmaceutical practice. The active compound can be administered orally, parenterally or intravenously. For example, the active compound can be administered in tablet form with such excipients as lactose, sodium citrate, calcium carbonate or dicalcium phosphate. Various disintigrants such as starch, alginic acid or certain complex silicates together with lubricating agents such as magnesium sterate, sodium aryl sulfate or talc can be utilized. For oral administration in capsule form, suitable materials include lactose in high molecular weight polyethylene glycols. When utilizing aqueous suspension, the active compounds are combined with emulsifying and/or suspending agents. Liquid carriers can be employed such as ethanol, water, propylene glycol, glycerine, glycine or the like. For parenteral administration, solutions of the active compounds in combination with other solutes such as glucose or saline can be utilized. Such aqueous solutions should be suitably buffered in order to render them isotonic. The dosage requird to attain effective inhibition of TdT to prevent proliferation of lymphoblastic leukemia cells will depend primarily upon the condition of the patient being treated. General procedure comprises small dosages being administered initially with a gradual increase in dosage until an optimal level is determined for a particular patient. When the active compound is administered orally, generally larger quantities of the active compound will be required to produce the same level of inhibition of leukemia cell proliferation as produced by a smaller quantity administered parenterally. In general, from about 10 mg to about 500 mg, preferably between about 10 mg and about 250 mg of the active compound per kilogram of body weight administered in single or multiple dosage units effectively prevents or inhibits leukemia cell proliferation.

The preferred compounds of this invention are 6-(p-aminoanilo) uracil and 6-(p-methoxyanilo) uracil which are represented by the following formulae:

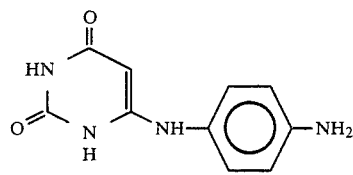

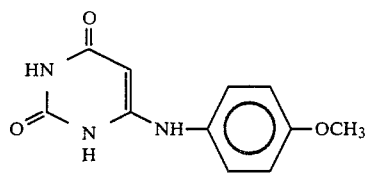

While the present invention has been described above with reference to the treatment of acute lymphoblastic leukemia, it is to be understood that the process of this invention also can be utilized to treat patients afflicted with other forms of leukemia which do not normally express TdT but which for the individual patient express TdT. For example, it has been found that approximately 10% of patients afflicted with acute myeloblastic leukemia have TdT positive cells. Slightly higher or lower percentages of TdT positive cells can be found in patients having acute undifferentiated leukemia, blast-chronic myelogenous leukemia, post-polycythemia vera leukemia, post-myeloid metaplasia leukemia or post-chemo/radiotherapy leukemia as shown in Table I.

TABLE I

| Occurence of Terminal Transferase in Leukemic Cells | | |
|---|---|---|
| Clinical Diagnosis | No. of Cases | No. TdT-Positive |
| Acute lymphoblastic leukemia | 300 | 290 |
| Acute myeloblastic leukemia | 120 | 10 |
| Acute undifferentiated leukemia | 30 | 16 |
| Blast-chronic myelogenous leukemia | 100 | 38 |
| Post-polycythemia vera leukemia | 15 | 3 |
| Post-myeloid metaplasia leukemia | 16 | 10 |
| Post chemo/radiotherapy leukemia | 9 | 2 |
| Stable phase chronic myelogenous leukemia | 30 | 0 |
| B-cell chronic lymphocytic leukemia | 15 | 0 |
| T-cell chronic lymphocytic leukemia | 3 | 0 |
| Sezary syndrome | 6 | 0 |
| Hairy cell leukemia | 9 | 0 |
| Multiple myeloma | 7 | 0 |

It is to be understood that the active compounds of this invention can be administered either as the compound or in any other pharmaceutically acceptable form such as the sodium salt form or any other salt form.

The following examples illustrate the present invention and are not intended to limit the same.

EXAMPLE I

This example illustrates a mwethod of making 6-(p-aminoanilo) racil. 1.3 grams monoacetylamiline $HCl_4$, 0.5 grams 6-chlorouracil and 0.9 grams sodium acetate were mixed in 15 ml glycine and were refluxed for 4 hours. 0.8 grams of the solid product 6-acetamidilanilino uracil were recovered. 0.5 grams of this product were mixed with 50 ml of 2.5 moles NaOH and were mixed for 15 minutes at room temperature. 0.4 grams (90% yield) of 6-(p-aminoanilo) uracil was recovered by filtration.

EXAMPLE II

This example illustrates a method for producing 6-(p-methoxyanilo) uracil. 0.5 grams 6-chlorouracil and 0.9 rams p-methoxyaniline were refluxed in 15 ml gylcine for 4 hours. The product was recovered by filtration at a 94% yield.

EXAMPLE III

This example illustrates the inhibiting effect of 6-(p-aminoanilo) uracil and 6-(p-methoxyanilo) uracil on TdT activity.

TdT was purified from normal calf thymus gland by a procedure utilizing the successive steps of homogenization, ion exchange chronology and gel filtration. Bollum et al, "The Enzymes", (R. D. Boxer Ed.) pp. 145–171, Academic Press, New York. TdT was assayed at 35° C. for 1 hour in 0.1 ml total volume of a reaction mixture comprising 0.05 M Tris-HCl (pH 8.3), 2 mM DDT, 0.6 mM $MnCl_2$, 10 μg bovine serum albumin (BSA), 1 μg $oligodA_{14-18}$, 10 μM $^3H$-dGTP (d-triphosphate) and chelex distilled $H_2O$. When used, the 6-anilinouracil derivates were added at various concentrations in 5 μl DMSO per 100 μl reaction mix. Other DNA polymerases ($\alpha$, $\beta$, and $\gamma$) were assayed using standard assay conditions, as previously described by Wright, Baril and Brown, Nucleic Acids Research, Vol. 8, No. 1, pp. 99-109, 1980.

Inhibition of Tdt-positive Cell Proliferation:

HeLa cells, El-4cells, L1210 cells were grown in suspended cell culture under standard conditions in RPMI medium, at 37° C. in moist air containing 5% $CO_2$. The characteristics of these cells are shown in Table II. All inhibitions were performed using a final concentration of 1% DMSO as inhibitor solvent. Control cells were therefore grown in the presence of 1% DMSO.

TABLE II

| Cell Line | Source | Tdt Status |
|---|---|---|
| HeLa | Human | Negative |
| L1210 | Mouse | Negative |
| EL-4 | Mouse | Positive |

Compound GW18C (6-(p-aminoanilo) uracil) was prepared as a 40 mM stock solution in pre-heated DMSO. This stock solution was progressively diluted to give a range of operating inhibitory concentrations between $1 \times 10^{-9}$ M and $1 \times 10^{-2}$ M. Inhibition was measured by comparing the number of viable cells in control cultures at the end of 72 hours with the number in cultures exposed to inhibitor. The compound was prepared as follows:

Inhibition of Purifed TdT:

Using the following standard reaction conditions, the several uracil analogues showed no TdT inhibition at 200 μM concentration (Table III). Reaction conditions used were as noted above.

TABLE III

| Designator | Compound | CMP 3H—dGMP inc. |
|---|---|---|
| Control (DMSO only) | | 12,131 |
| GW-9E | 6-anilinouracil | 10,350 |
| GW-7B | 6-(benzylamino)uracil | 12,780 |
| GW-7C | 6-(phenethylamino)uracil | 12,391 |
| GW-11D | 6-(p-butylanilino)uracil | 10,925 |
| GW-22E | 6-(p-hydroxyanilino)uracil | 21,760 |
| GW-16C | 6-(p-acetamidobenzylamino)uracil | 14,160 |
| GW-18B | 6-(cyclohexylamino)uracil | 13,442 |
| GW-20B | 6-(cyclohexylmethylamino)uracil | 11,296 |
| GW-18E | 6-(n-pentylamino)uracil | 11,674 |
| GW-17B | 6-(3',4'-trimethyleneanilino)uracil | 12,383 |
| GW-22A | 6-(iso-pentylamino)uracil | 12,005 |
| GW-28A | 6-(d-naphthylamino)uracil | 12,038 |
| GW-33E | 6-(p-methoxybenzyl)-6-aminouracil | 11,988 |

In contrast, two other analogues showed significant inhibition of TdT:

| Designator | Compound | CMP $^3$H—dGMP inc. |
|---|---|---|
| Control (DMSO only) | | 12,131 |
| GW-18C | 6-(p-aminoanilo)uracil | 5,198 |
| GW-17E | 6-(p-methoxyanilo)uracil | 6,980 |

Substitution in the para-position of the phenyl ring appears to be critical. Compounds GW-23A and GW-28D are not inhibitory and are structurally similar except for the substitution on the phenyl ring:

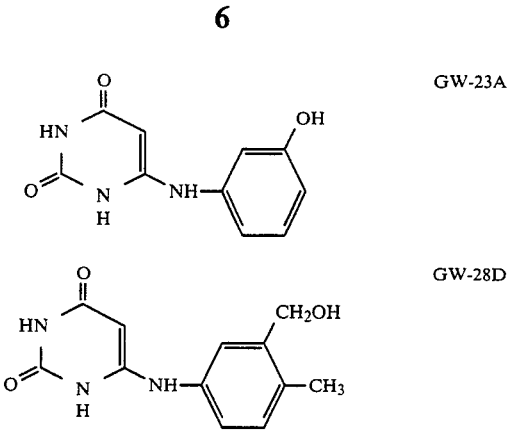

The inhibition curves for 6-(p-methoxyanilo) uracil (GW-17E) and 6-(p-animoanilo) uracil (GW-18C) are shown in FIG. I.

The effect of GW-17E and GW-18C of TdT activity is specific. HeLa cell polymerase $\alpha$, $\beta$ and $\gamma$ are not effected at 400 μM concentrations (Table IV):

TABLE IV

| Additive | CMP Incorporated Enzymes | | | |
|---|---|---|---|---|
| (at 400 M) | Pol $\alpha$ | Pol $\beta$ | Pol $\gamma$ | TdT |
| DMSO Control | 15,040 | 5,221 | 7,490 | 12,131 |
| GW-17E | 15,217 | 5,492 | 7,223 | 4,964 |
| GW-18C | 15,417 | 5,218 | 7,165 | 3,102 |

Inhibition of Cell Proliferation

Growth of HeLa cells and L1210 cells are not inhibited by GW-18C even at 400 μM concentrations. Both of these lines are TdT-negative. In contrast, at 400 μM concentrations, GW-18C inhibited the TdT-positive line EL-4 proliferation. A dose response curve was seen, with maximal (80%) growth inhibition at 72 hours at 400 μM concentrations.

The data show that certain types of substituted 6-anilinouracils can specifically inhibit TdT activity and retard the growth of TdT-positive cells in culture. This drug-induced inhibition of both TdT activity and growth of TdT-positive cells shows that members of this class of substituted 6-anilinouracils will have utility in the clinical treatment of TdT-positive human and animal neoplastic disease. In addition, these inhibitory agents can be used to dissect out the function of TdT in normal lymphoid cell ontogeny.

We show that the introduction of either an amino or O-methyl group into the para-position of the phenyl ring produces compounds which are specific, potent inhibitors of the TdT enzyme. An important conclusion of this work is that any substitution at the para-phenyl position as defined above should have TdT specificity.

In one aspect of this invention, a patient can be treated by removing a sample of the patient's bone marrow cells and incubating it with the compounds of this invention in order to deactivate TdT. The cells then are stored at about $-10°$ C. and exposed to a lethal dose of radiation. The cells then are reintroduced into the patient's marrow. This general procedure is known as autologous marrow infusion and is well known in the art.

We claim:

1. A process for treating a human patient afflicted with a form of leukemia, the cells of which express terminal deoxynucleotidyl transferase, which comprises administering to the patient a compound of the formula:

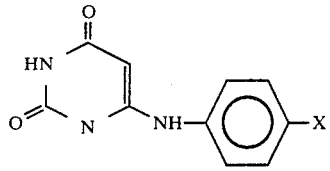

wherein X is $C_1$–$C_{10}$ alkoxy or amino and is effective for the selective inhibition of terminal deoxynucleotidyl transferase in an amount effective to prevent proliferation of said cells in vivo.

2. A process for treating a human patient afflicted with a form of leukemia, the cells of which express terminal deoxynucleotidyl transferase which comprises administering to the patient a compound comprising the formula 6-(p-aminoanilo) uracil for the selective inhibition of terminal deoxynucleoticdy transferase in an amount effective to prevent proliferation of said cells in vivo.

3. A process for treating a human patient afflicted with a form of leukemia, the cells of which express terminal deoxynucleotidyl transferase, which comprises administering to the patient a compound comprising the formula 6-(p-methoxyanilo) uracil for the selective inhibition of terminal deoxynucleotidyl transferase in an amount effective to prevent proliferation of said cells in vivo.

4. The process of claim 1, 2 or 3 wherein the compound further comprises a pharmaceutically acceptable form thereof.

* * * * *